US012788461B2

(12) United States Patent
Tempco et al.

(10) Patent No.: US 12,788,461 B2
(45) **Date of Patent: *Nov. 10, 2026**

(54) BONE SCREW AND METHOD OF MANUFACTURE

(71) Applicant: Warsaw Orthopedic, Inc., Warsaw, IN (US)

(72) Inventors: Dale A. Tempco, Germantown, TN (US); Rodney Ray Ballard, Lakeland, TN (US); Keith E. Miller, Germantown, TN (US); William Alan Rezach, Covington, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/965,913

(22) Filed: Dec. 2, 2024

(65) Prior Publication Data

US 2025/0090209 A1 Mar. 20, 2025

Related U.S. Application Data

(63) Continuation of application No. 18/538,384, filed on Dec. 13, 2023, now Pat. No. 12,185,998, which is a (Continued)

(51) Int. Cl.
*A61B 17/86* (2006.01)
*A61B 17/70* (2006.01)
*A61B 17/00* (2006.01)

(52) U.S. Cl.
CPC ...... *A61B 17/8625* (2013.01); *A61B 17/7059* (2013.01); *A61B 17/866* (2013.01); (Continued)

(58) Field of Classification Search
CPC ... A61B 17/86; A61B 17/8625; A61B 17/866; A61B 17/7059; A61B 17/7001; A61B 2017/00526; A61B 2017/00862
(Continued)

(56) References Cited

U.S. PATENT DOCUMENTS 5,743,914 A 4/1998 Skiba
5,964,768 A * 10/1999 Huebner .............. A61B 17/863 606/65
(Continued)

FOREIGN PATENT DOCUMENTS

CN 2829653 10/2006
CN 102137627 7/2011
(Continued)

OTHER PUBLICATIONS

"Commercialization Solutions for the Orthopaedic Industry," BONEZONE, vol. 16, No. 3, Aug. 2017, 52 pages.
(Continued)

*Primary Examiner* — Jessica Weiss
(74) *Attorney, Agent, or Firm* — Sheridan Ross P.C.

(57) ABSTRACT

A bone screw comprises a shaft defining a longitudinal axis and a minor diameter. The shaft including a core having an angled surface relative to the axis. The angled surface extending from the minor diameter adjacent a proximal portion of the shaft to a distal portion of the shaft, and a wall disposed about the angled surface. The wall including at least one thread having an external thread form. In some embodiments, systems, spinal constructs, surgical instruments and methods are disclosed.

19 Claims, 5 Drawing Sheets

Related U.S. Application Data continuation of application No. 17/543,865, filed on Dec. 7, 2021, now Pat. No. 11,857,233, which is a continuation of application No. 15/975,389, filed on May 9, 2018, now Pat. No. 11,224,470.

(52) U.S. Cl.
CPC ............... *A61B 2017/00526* (2013.01); *A61B 2017/00862* (2013.01); *A61B 17/7001* (2013.01)

(58) Field of Classification Search
USPC .................................................. 606/300–321
See application file for complete search history.

(56) References Cited

U.S. PATENT DOCUMENTS 7,850,717 B2 * 12/2010 Dewey ............... A61B 17/8625 606/76
7,892,265 B2 * 2/2011 Perez-Cruet ....... A61B 17/7025 606/301
7,892,267 B2 * 2/2011 Lancial .............. A61B 17/8685 606/300
10,307,194 B2 6/2019 Tempco
10,575,886 B2 3/2020 Tempco et al.
10,864,602 B2 * 12/2020 Tempco .................. B22F 7/062
10,993,754 B2 5/2021 Kuntz et al.
11,224,470 B2 1/2022 Tempco et al.
11,229,465 B2 1/2022 Tempco
11,589,907 B2 2/2023 Tempco et al.
11,857,233 B2 1/2024 Tempco et al.
12,185,998 B2 1/2025 Tempco et al.
2002/0055742 A1 5/2002 Lieberman
2002/0123752 A1 * 9/2002 Schultheiss ........ A61B 17/8685 606/92
2003/0125744 A1 7/2003 Contiliano et al.
2006/0111715 A1 * 5/2006 Jackson ............. A61B 17/7032 606/279
2006/0142772 A1 6/2006 Ralph et al.
2007/0065779 A1 * 3/2007 Mangano ........... A61C 13/0018 433/201.1
2007/0233071 A1 * 10/2007 Dewey ................. A61B 17/866 606/86 A
2008/0134411 A1 6/2008 Shapiro
2008/0177331 A1 7/2008 Perez-Cruet et al.
2008/0249574 A1 10/2008 McCombs et al.
2008/0249579 A1 * 10/2008 Taylor .................. A61B 17/863 606/301
2009/0018592 A1 1/2009 Pitbladdo
2009/0093888 A1 * 4/2009 Dawson ................ A61L 31/121 606/301
2010/0042167 A1 2/2010 Nebosky et al.
2010/0094420 A1 * 4/2010 Grohowski, Jr. ......... B22F 3/16 623/16.11
2010/0145393 A1 * 6/2010 Fallin ................... A61C 8/0016 606/301
2011/0172798 A1 7/2011 Staiger et al.
2011/0319946 A1 * 12/2011 Levy .................. A61B 17/8685 606/300
2012/0197309 A1 * 8/2012 Steele ................ A61B 17/7041 606/301
2013/0178900 A1 7/2013 Fallin et al.
2014/0012334 A1 * 1/2014 Armstrong ........... A61B 17/863 606/312
2014/0046381 A1 2/2014 Asfora
2015/0018956 A1 * 1/2015 Steinmann ................ A61F 2/34 419/53
2015/0032159 A1 1/2015 Beger et al.
2015/0046379 A1 2/2015 Cantin et al.
2015/0127057 A1 5/2015 Ganey
2015/0223907 A1 8/2015 Kieser
2015/0250513 A1 9/2015 De Lavigne Sainte Suzanne
2015/0313658 A1 11/2015 Kolb
2016/0100870 A1 4/2016 Lavigne et al.
2016/0157908 A1 * 6/2016 Cawley ................. A61F 2/3094 606/301
2016/0166301 A1 6/2016 Papangelou et al.
2016/0367371 A1 12/2016 De Beaubien et al.
2017/0165077 A1 6/2017 McDonnell
2017/0245851 A1 8/2017 Biedermann et al.
2018/0028242 A1 2/2018 Parekh et al.
2018/0042646 A1 * 2/2018 Frey ...................... A61F 2/4611
2018/0042702 A1 2/2018 Stuebinger et al.
2023/0190349 A1 6/2023 Tempco et al.

FOREIGN PATENT DOCUMENTS

CN 104523342 4/2015
CN 204337022 5/2015
CN 204337069 5/2015
CN 104758042 7/2015
CN 104825220 8/2015
CN 104840243 8/2015
CN 204581484 8/2015
CN 105193489 12/2015
CN 204931871 1/2016
CN 204931872 1/2016
CN 205007020 2/2016
CN 105662621 6/2016
CN 205698065 11/2016
CN 106473787 3/2017
CN 106580494 4/2017
CN 106859792 6/2017
CN 206576968 10/2017
CN 206761724 12/2017
CN 206761725 12/2017
CN 206761797 12/2017
CN 206761967 12/2017
EP 2796104 10/2014
FR 3036945 12/2016
KR 10-2014-0141463 12/2014
WO WO 2008/134411 11/2008
WO WO 2014/076157 5/2014
WO WO 2016/099620 6/2016
WO WO 2017/161115 9/2017
WO WO 2017/161121 9/2017
WO WO 2017/192853 11/2017

OTHER PUBLICATIONS

Douville et al., "News Release: AmorChem invests in a novel titanium porous compression screw for bone fixation and puts in place a Master Agreement with McGill," AmorChem & McGill University Research Institute, Dec. 21, 2012, retrieved from http://amorchem.com/wp-content/uploads/Dec-21-2012-AmorChem-Porous-screw-Press-Release-ENG_FOR-RELEASE.pdf, 2 pages.
Official Action for U.S. Appl. No. 15/975,203, dated Oct. 16, 2018, 9 pages.
Official Action for U.S. Appl. No. 15/975,203, dated May 24, 2019, 13 pages.
Notice of Allowance for U.S. Appl. No. 15/975,203, dated Nov. 1, 2019, 6 pages.
Official Action for U.S. Appl. No. 16/804,763, dated Dec. 1, 2021, 8 pages.
Official Action for U.S. Appl. No. 16/804,763, dated May 12, 2022, 10 pages.
Notice of Allowance for U.S. Appl. No. 16/804,763, dated Sep. 14, 2022, 10 pages.
Official Action for U.S. Appl. No. 18/109,452, dated Sep. 4, 2024, 14 pages.
Notice of Allowance for U.S. Appl. No. 18/109,452, dated Dec. 2, 2024, 6 pages.
Official Action for U.S. Appl. No. 15/975,389, dated Mar. 20, 2020, 16 pages.
Official Action for U.S. Appl. No. 15/975,389, dated Sep. 14, 2020, 16 pages.
Official Action for U.S. Appl. No. 15/975,389, dated May 25, 2021, 12 pages.

(56) References Cited

OTHER PUBLICATIONS

Notice of Allowance for U.S. Appl. No. 15/975,389, dated Sep. 9, 2021, 9 pages.
Official Action for U.S. Appl. No. 17/543,865, dated Feb. 13, 2023, 29 pages.
Notice of Allowance for U.S. Appl. No. 17/543,865, dated Aug. 23, 2023, 11 pages.
Notice of Allowance for U.S. Appl. No. 18/538,384, dated Sep. 3, 2024, 10 pages.

* cited by examiner

BONE SCREW AND METHOD OF MANUFACTURE

This U.S. Non-Provisional patent application is a Continuation of and claims the benefit of priority from U.S. Non-Provisional patent application Ser. No. 18/538,384, filed on Dec. 13, 2023, which is a Continuation of and claims the benefit of priority from U.S. Non-Provisional patent application Ser. No. 17/543,865, filed on Dec. 7, 2021, issued as U.S. Pat. No. 11,857,233, which is a Continuation of and claims the benefit of priority from U.S. Non-Provisional patent application Ser. No. 15/975,389, filed on May 9, 2018, issued as U.S. Pat. No. 11,224,470, the entire disclosures of which are hereby incorporated by reference.

TECHNICAL FIELD

The present disclosure generally relates to medical devices for the treatment of spinal disorders, and more particularly to a spinal implant system having spinal implants manufactured by a method including a plurality of manufacturing techniques.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including bone fasteners are often used to provide stability to a treated region. Such bone fasteners are traditionally manufactured using a medical machining technique. This disclosure describes an improvement over these prior technologies.

SUMMARY

In one embodiment, a bone screw is provided. The bone screw comprises a shaft defining a longitudinal axis and a minor diameter. The shaft including a core having an angled surface relative to the axis. The angled surface extending from the minor diameter adjacent a proximal portion of the shaft to a distal portion of the shaft, and a wall disposed about the angled surface. The wall including at least one thread having an external thread form. In some embodiments, systems, spinal constructs, spinal implants, surgical instruments and methods are disclosed.

In one embodiment, the bone screw comprises a shaft defining a longitudinal axis and a minor diameter. The shaft including a core having an angled surface relative to the axis. The angled surface extending from the minor diameter adjacent a proximal portion of the shaft to a distal portion of the shaft, and a wall disposed about the angled surface. The wall including at least one thread having an external thread form. The thread form along a proximal portion of the wall includes a solid configuration relative to the thread form along a distal portion of the wall.

In one embodiment, the bone screw comprises a shaft defining a longitudinal axis and a minor diameter. The shaft including a core having an angled surface relative to the axis, the angled surface extending from the minor diameter adjacent a proximal portion of the shaft to a distal portion of the shaft, and a wall disposed about the angled surface. The wall including at least one thread having an external thread form. The proximal portion being formed by a subtractive, deformative or transformative manufacturing method to include a first thread form and define a distal end. The distal portion being formed onto the distal end in a layer by layer formation by an additive manufacturing method, the distal portion including a core having an angled surface relative to the axis and a wall disposed about the angled surface. The wall including at least one thread having an external thread form.

BRIEF DESCRIPTION OF THE DRAWINGS

The present disclosure will become more readily apparent from the specific description accompanied by the following drawings, in which.

DETAILED DESCRIPTION

Figure 1:
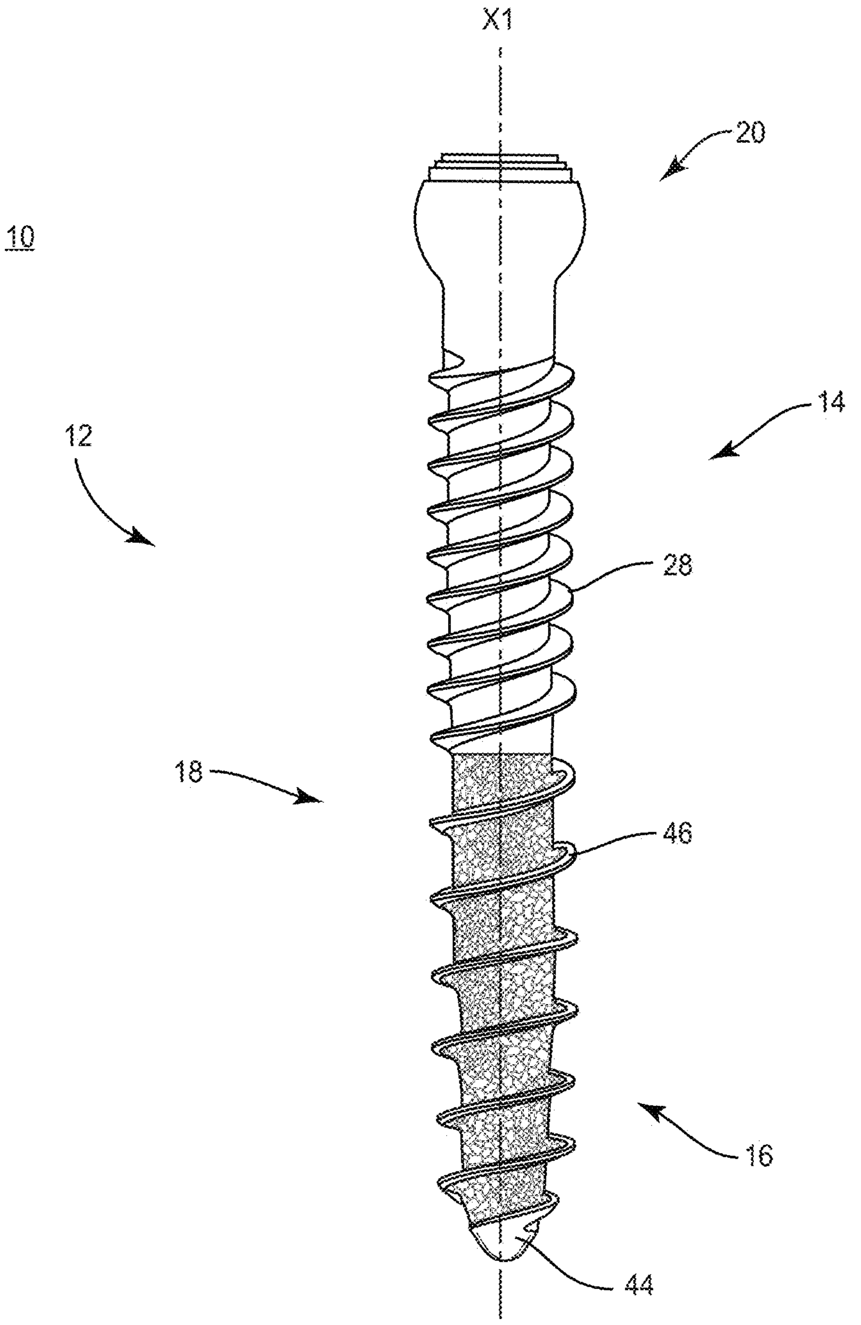
FIG. 1 is a side view of components of one embodiment of a system in accordance with the principles of the present disclosure.

The exemplary embodiments of a surgical system and related methods of use disclosed are discussed in terms of medical devices for the treatment of musculoskeletal disorders and more particularly, in terms of a spinal implant having a structurally optimized internal structure to enhance the mechanical properties of the bone screw.

In some embodiments, the spinal implant system of the present disclosure comprises a bone screw having internal features to structurally optimize the mechanical properties of the bone screw that combines a manufacturing method, such as, for example, one or more traditional manufacturing features and materials and a manufacturing method, such as, for example, one or more additive manufacturing features and materials. In some embodiments, the bone screw is configured with internal features, such as, for example, various forms and/or patterns. In some embodiments, the internal features may be homogeneous. In some embodiments, the internal features are configured to optimize bone screw function by increasing bone screw rigidity and/or increasing bone screw strength. In some embodiments, the internal features are configured to provide deflection in selected areas of the bone screw.

In some embodiments, the spinal implant system of the present disclosure comprises a bone screw having a solid core that includes a varied configuration to optimize bone screw function. In some embodiments, the features of the bone screw can be created and/or altered through additive manufacturing. In some embodiments, the features can be manufactured to minimize material usage. In some embodiments, the configuration of the solid core is configured to provide deflection in selected areas of the bone screw. In some embodiments, the bone screw includes features, such as, for example, struts, braces and/or honeycomb patterns of material within the body of the bone screw. In some embodiments, the features include porous and/or trabecular material. In some embodiments, the bone screw includes an internal solid strut configured to reinforce a load bearing portion of the bone screw.

In some embodiments, the spinal implant system of the present disclosure is configured to enhance fixation of bone screws with bone. In some embodiments, the spinal implant system of the present disclosure includes a spinal implant configured for engagement with cortical bone and cancellous bone within the vertebra. In some embodiments, the spinal implant system of the present disclosure is configured to resist and/or prevent toggle on a bone screw when the bone screw is engaged with dense cortical bone and a less dense cancellous bone resulting from a load on the bone screw. In some embodiments, the spinal implant system of the present disclosure is configured to resist and/or prevent loosening of the bone screw from the cortical bone and in some instances, pull out from the vertebra. In some embodiments, the spinal implant system of the present disclosure is configured to facilitate bone through-growth to provide for an improved bone attachment to the bone screw. In some embodiments, the bone screw is anchored in the bone thereby reducing pull out.

In some embodiments, the spinal implant system comprises a spinal implant having a hybrid configuration that combines a manufacturing method, such as, for example, one or more traditional manufacturing features and materials and a manufacturing method, such as, for example, one or more additive manufacturing features and materials. In some embodiments, additive manufacturing includes 3-D printing. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing and on-demand manufacturing. In some embodiments, the spinal implant system comprises a spinal implant being manufactured by a fully additive process and grown or otherwise printed.

In some embodiments, the spinal implant system of the present disclosure comprises a spinal implant, such as, for example, a bone screw manufactured by combining traditional manufacturing methods and additive manufacturing methods. In some embodiments, the bone screw is manufactured by applying additive manufacturing material in areas where the bone screw can benefit from materials and properties of additive manufacturing. In some embodiments, traditional materials are utilized where the benefits of these materials, such as physical properties and cost, are superior to those resulting from additive manufacturing features and materials.

In some embodiments, the spinal implants, surgical instruments and/or medical devices of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the spinal implants, surgical instruments and/or medical devices of the present disclosure may be employed with other osteal and bone related applications, including those associated with diagnostics and therapeutics. In some embodiments, the spinal implants, surgical instruments and/or medical devices of the present disclosure may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions such as maxillofacial and extremities. The spinal implants, surgical instruments and/or medical devices of the present disclosure may also be alternatively employed with procedures for treating the lumbar, cervical, thoracic, sacral and pelvic regions of a spinal column. The spinal implants, surgical instruments and/or medical devices of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term “tissue” includes soft tissue, ligaments, tendons, cartilage and/or bone unless specifically referred to otherwise.

Figure 2:
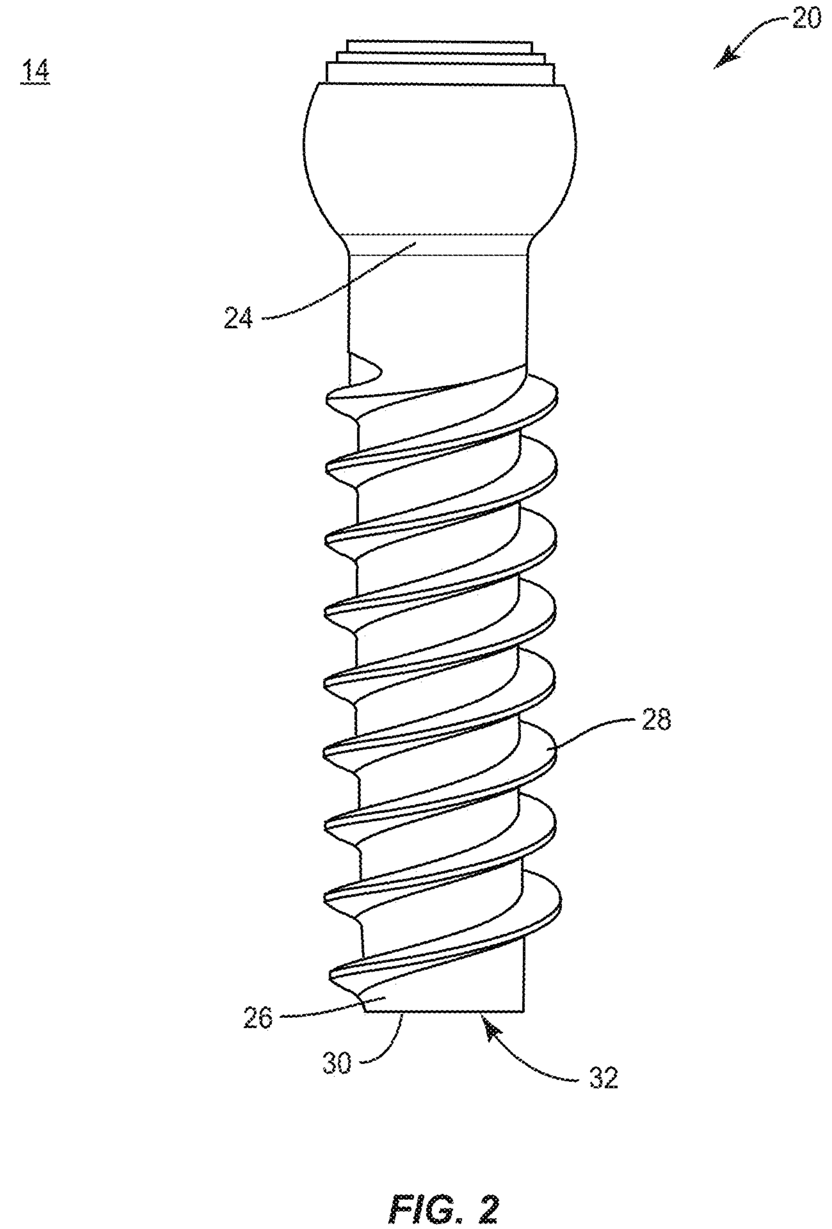
FIG. 2 is a side view of components of the system shown in FIG. 1.
Figure 3:
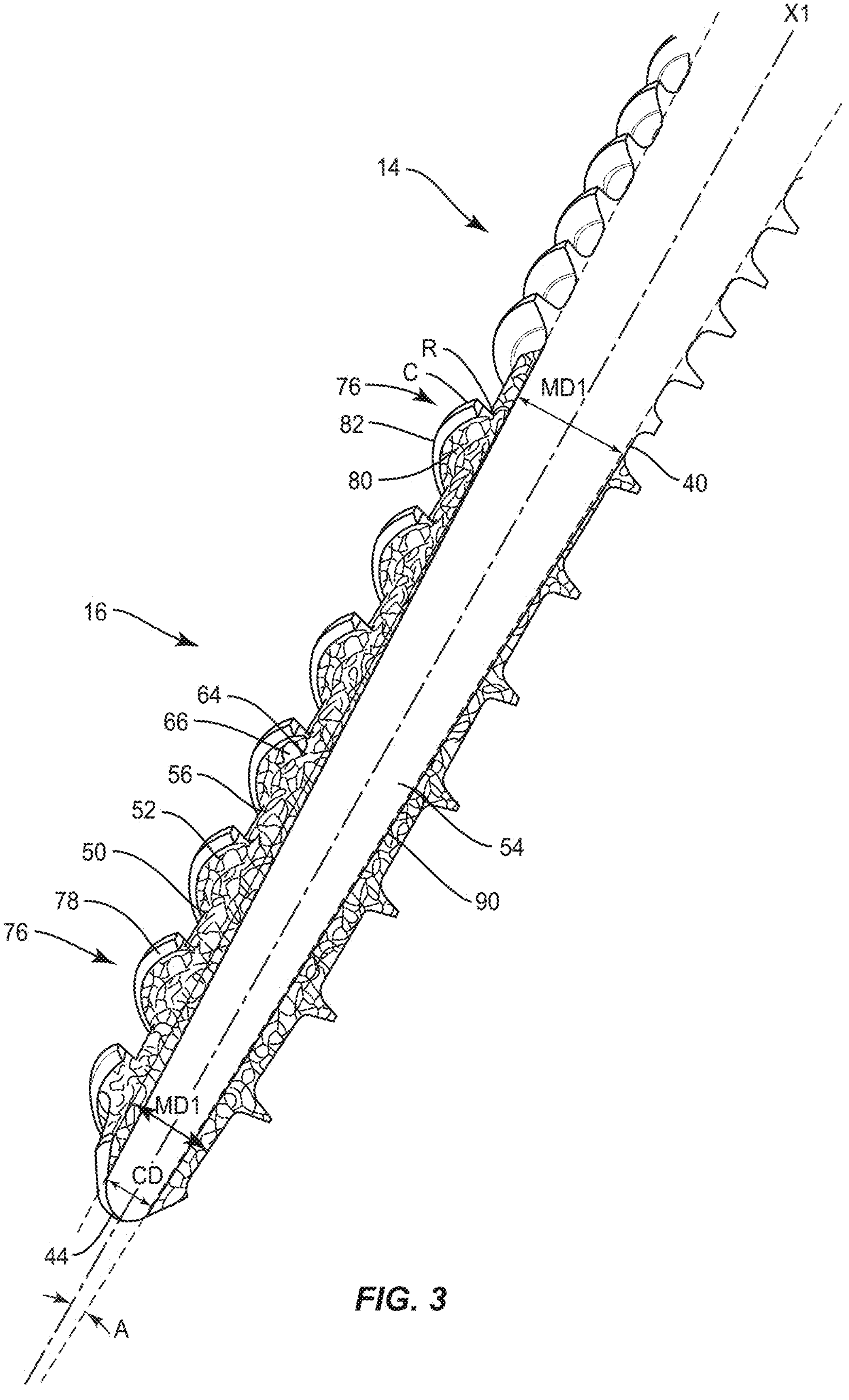
FIG. 3 is a side cross section view of components of the system shown in FIG. 1.

The following discussion includes a description of a spinal implant, a method of manufacturing a spinal implant, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-3, there are illustrated components of a spinal implant system 10 including spinal implants, surgical instruments and medical devices.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant comprising a bone fastener, such as, for example, a bone screw 12. In some embodiments, bone screw 12 includes variable, alternate, different and/or transition portions to optimize bone growth and/or fixation with tissue. In some embodiments, the portions of bone screw 12 can include a variable inner core. In some embodiments, the inner core is tapered to selectively provide a point of controlled deflection within bone screw 12 to resist and/or prevent pull out, toggle or fatigue fracture of bone screw 12. In some embodiments, the portions of bone screw 12 can include an internal solid strut. In some embodiments, the portions of bone screw 12 can include a variable section thread and a solid strut. In some embodiments, the portions of bone screw 12 can include one or more cavities, for example, one or more pathways, openings, lattice and/or scaffold. In some embodiments, bone screw 12 can include even, uninterrupted portions, portions that are continuous and without cavity and/or solid portions. In some embodiments, bone screw 12 can include roughened portions, porous portions, trabecular portions and/or honeycomb portions. In some embodiments, bone screw 12 can include roughened portions, porous portions, trabecular portions and/or honeycomb portions. In some embodiments, bone screw 12 allows bone growth therethrough such that bone is allowed to connect through bone screw 12.

Bone screw 12 defines a longitudinal axis X1. Bone screw 12 includes a screw shaft 18 having a proximal portion 14 and a distal portion 16. In some embodiments, bone screw 12 is manufactured by a manufacturing process to enhance fixation and/or facilitate bone growth, as described herein. In some embodiments, bone screw 12 is manufactured by an additive manufacturing method. In some embodiments, proximal portion 14 is fabricated by a first manufacturing method and distal portion 16 fabricated by a second manufacturing method to enhance fixation and/or facilitate bone growth, as described herein.

In some embodiments, the manufacturing method can include a traditional machining method, such as, for example, subtractive, deformative or transformative manufacturing methods. In some embodiments, the traditional manufacturing method may include cutting, grinding, rolling, forming, molding, casting, forging, extruding, whirling, grinding and/or cold working. In some embodiments, the traditional manufacturing method includes portion 14 being formed by a medical machining process. In some embodiments, medical machining processes can include use of computer numerical control (CNC) high speed milling machines, Swiss machining devices, CNC turning with living tooling and/or wire EDM 4th axis. In some embodiments, the manufacturing method for fabricating portion 14 includes a finishing process, such as, for example, laser marking, tumble blasting, bead blasting, micro blasting and/or powder blasting.

For example, portion 14 is formed by a manufacturing method, which includes feeding a wire, rod, bar, or wire or rod bar stock into a machine that cuts the wire at a designated length to form a screw blank and then forms a head of the screw blank into a selected configuration. Portion 14 is manufactured to include a head 20 and a portion of screw shaft 18. Portion 14 extends between an end 24 and an end 26. End 24 includes head 20.

Portion 14 includes threads 28, which are fabricated by traditional machining methods, as described herein. Threads 28 extend along all or a portion of portion 14. Threads 28 are oriented with portion 14 and disposed for engagement with tissue. In some embodiments, threads 28 include a fine, closely-spaced configuration and/or shallow configuration to facilitate and/or enhance engagement with tissue. In some embodiments, threads 28 include a smaller pitch or more thread turns per axial distance to provide a stronger fixation with tissue and/or resist loosening from tissue. In some embodiments, threads 28 include an increased greater pitch and an equal lead between thread turns. In some embodiments, threads 28 are continuous along portion 14. In some embodiments, threads 28 are continuous along shaft 18 via a second manufacturing method, as described herein. In some embodiments, threads 28 may be intermittent, staggered, discontinuous and/or may include a single thread turn or a plurality of discrete threads. In some embodiments, other penetrating elements may be located on and/or manufactured with portion 14, such as, for example, a nail configuration, barbs, expanding elements, raised elements, ribs, and/or spikes to facilitate engagement of portion 14 with tissue.

End 26 includes a surface 30 that defines a distal end 32. In some embodiments, surface 30 may be disposed along a length of portion 14 or at a distalmost surface of portion 14. In some embodiments, distal end 32 extends perpendicular to axis X1. In some embodiments, distal end 32 may be disposed in various orientations relative to axis X1, such as, for example, transverse and/or at angular orientations, such as acute or obtuse. In one embodiment, distal end 32 is disposed at an acute angular orientation relative to axis X1.

Distal end 32 is configured for providing a fabrication platform for forming portion 16 thereon with an additive manufacturing method, as described herein. Distal end 32 has a substantially planar configuration for material deposition and/or heating during an additive manufacturing process for fabricating portion 16 onto distal end 32. In some embodiments, all or only a portion of distal end 32 may have alternate surface configurations, such as, for example, angled, irregular, uniform, non-uniform, offset, staggered, tapered, arcuate, undulating, mesh, porous, semi-porous, dimpled, pointed and/or textured. In some embodiments, distal end 32 may include a nail configuration, barbs, expanding elements, raised elements, ribs, and/or spikes to provide a fabrication platform for forming portion 16 thereon with an additive manufacturing method, as described herein. In some embodiments, all or only a portion of distal end 32 may have alternate cross section configurations, such as, for example, oval, oblong triangular, square, polygonal, irregular, uniform, non-uniform, offset, staggered, and/or tapered.

Turning to FIG. 3, portion 16 is fabricated with a second manufacturing method by disposing a material onto distal end 32, as described herein. Portion 16 is configured for fabrication on distal end 32 such that portion 16 is fused with surface 30. Portion 16 is formed on distal end 32 by an additive manufacturing method. Portion 16 is formed on distal end 32 to extend between an end 40 and end 42 according to instructions received from the computer and processor, and end 40 is fused with surface 30. Portion 16 is fabricated according to instructions received from the computer and processor based on the digital rendering and/or data of the selected configuration, via the additive manufacturing process described herein to include a thread 76 that extends between end 40 and a distal tip 44. In some embodiments, portion 14 is formed on an end of portion 16. In some embodiments, portion 14 is formed on an end of head 20.

Portion 16 includes a wall 50 having a surface 52. In some embodiments, wall 50 extends circumferentially to define portion 16. In some embodiments, wall 50 is disposed about an inner core 54, as described herein. In various embodiments, inner core 54 has a variable configuration, as described herein. In some embodiments, wall 50 defines a thickness, which may be uniform, undulating, tapered, increasing, decreasing, variable, offset, stepped, arcuate, angled and/or staggered. In some embodiments, surface 52 may be rough, textured, porous, semi-porous, dimpled, knurled, toothed, grooved and/or polished.

Core 54 has a variable configuration and includes a tapered surface 90 to facilitate fixation with tissue. Surface 90 is angled at an angle A relative to axis X1. In various embodiments, surface 90 extends from a minor diameter MD1 of screw 12. In some embodiments, surface 90 starts to extend from minor diameter MD1 at or adjacent where proximal portion 14 meets the distal portion 16. In various embodiments, the surface 90 extends from the minor diameter, distally, through distal portion 16. Surface 90 extends along all or a portion of core 54. Surface 90 is angled relative to axis X1 to define a tapered cross section. In some embodiments, surface 90 is uniformly tapered. In a contemplated embodiment, the surface 90 does not taper uniformly, such as by angle A being different along various points along the screw 12. Variables for a designer to consider in determining whether and how to taper include a balance between any of strength for insertion of the screw 12 (e.g., torque strength), strength against breaking after implanted, and non-solid real estate for promoting bone growth into the screw (i.e., into lattice 56. As an example, a designer may determine that core 54 being thicker proximally by a certain amount versus distally is appropriate to provide sufficient strength for insertion, wherein more strength may be determined needed in more proximal portions of the screw 12 than distally, where less strength is needed, and more lattice can be provided for more bone growth after implantation. Other variables include other supporting structure 12 of the screw, such as configuration of the thread form, such as whether fully or partially solid or non-solid. Other varying core widths, shapes, and angling can similarly be determined preferable to balance any of these or other such variables. In some embodiments, surface 90 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, surface 90 defines a cross section of core 54 that decreases in diameter CD from end 40 to distal tip 44. In a contemplated embodiment, the core 54 tapers distally toward the tip 44 to a zero or near-zero diameter. In some embodiments, surface 90 defines a cross section of core 54 that increases distally in diameter.

Core 54 is configured to provide a selected point of deflection within bone screw 12. For example, bone screws 12 are subjected to various loads when implanted with tissue, such as, for example, vertebrae. Core 54 is tapered to optimize the deflection of bone screw 12 when under loads, for example, an axial load or a cantilever load applied by vertebrae to resist and/or prevent pull-out. In some embodiments, core 54 is configured to provide an increased resistance to bending and/or lateral torsional buckling. In some embodiments, core 54 reduces the effects of shear stresses on bone screw 12. In some embodiments, core 54 is configured to reduce an angle of twist.

Core 54 extends within distal portion 16 and includes a solid configuration. In some embodiments, core 54 is continuous, or solid, without any internal openings and/or cavities. In some embodiments, core 54 includes a material having a closely compacted structure. In some embodiments, core 54 includes a solid configuration, which may include a range of density including 0.5 through 10.5 grams per cubic centimeter. In some embodiments, core 54 includes a density that is greater than a density of lattice 56.

In some embodiments, core 54 may include a porous configuration configured to facilitate bone growth. In some embodiments, the porous configuration may include a range of porosity over a wide range of effective pore sizes. In some embodiments, core 54 includes a trabecular configuration. In some embodiments, the trabecular configuration may include a density similar to cancellous or cortical bone tissue.

Surface 52 includes a non-solid configuration, such as, for example, a lattice 56. In some embodiments, the non-solid configuration may include a porous structure and/or a trabecular configuration. Disclosures herein involving a lattice, or other particular type of non-solid structure, are meant to disclose at the same time analogous embodiments in which other non-solid structure in addition or instead of the particular type of structure.

In various embodiments, the non-solid configuration is configured to provide one or a plurality of pathways to facilitate bone through growth within, and in some embodiments all of the way through, from one surface to an opposite surface of bone screw 12. Lattice 56 is continuous along surface 52 of portion 16 between end 40 and distal tip 44. In some embodiments, lattice 56 extends along all or a portion of inner core 54. Thread 46 is connected with lattice 56 to facilitate fixation of threads 46 with tissue. In some embodiments, lattice 56 may include one or more portions, layers and/or substrates. In some embodiments, one or more portions, layers and/or substrates of lattice 56 may be disposed side by side, offset, staggered, stepped, tapered, end to end, spaced apart, in series and/or in parallel. In some embodiments, lattice 56 defines a thickness, which may be uniform, undulating, tapered, increasing, decreasing, variable, offset, stepped, arcuate, angled and/or staggered. In some embodiments, one or more layers of lattice 56 are disposed in a side by side, parallel orientation within wall 50. Lattice 56 includes one or more layers of a matrix of material.

In some embodiments, lattice 56 includes a plurality of nodes 64 And openings 66, which can be disposed in rows and columns, and/or in a random configuration. In some embodiments, nodes 64 and openings 66 are disposed in a series orientation. In some embodiments, nodes 64 and openings 66 are disposed in a parallel orientation.

In some embodiments, lattice 56 may form a rasp-like configuration. In some embodiments, lattice 56 is configured to engage tissue, such as, for example, cortical bone and/or cancellous bone, such as, to cut, shave, shear, incise and/or disrupt such tissue. In some embodiments, all or a portion of each lattice 56 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, lattice 56 may be rough, textured, porous, semi-porous, dimpled, knurled, toothed, grooved and/or polished to facilitate engagement and cutting of tissue. In some embodiments, lattice 56 forms a tunnel configured to guide, drive and/or direct the cut tissue into openings 66 to facilitate fusion of bone screw 12 with tissue, such as, for example, vertebrae. In some embodiments, wall 50 includes a trabecular configuration.

Thread 76 has a variable configuration and includes an external thread form 78. Thread form 78 has a flank 79 extending between a root R and a crest C. Thread 76 includes an external thread form 78. Flank 79 has a variable configuration and includes a portion 80 and a portion 82 to facilitate bone growth and/or fixation with tissue. Portion 80 extends circumferentially about root R and includes a lattice configuration to facilitate fusion of bone screw 12 with tissue, as described herein. Portion 80 transitions from lattice 56 such that wall 50 and portion 82 are homogenous. In some embodiments, portion 80 includes a trabecular configuration. In some embodiments, the trabecular configuration may include a density similar to cancellous or cortical bone tissue. In some embodiments, portion 80 includes a porous configuration. In some embodiments, the porous configuration may include a range of porosity over a wide range of effective pore sizes. In some embodiments, the porous configuration of portion 16 may have macroporosity, mesoporosity, microporosity and nanoporosity.

A surface 88 of the lattice of portion 80 is configured to engage tissue, such as, for example, cortical bone and/or cancellous bone, such as, to cut, shave, shear, incise and/or disrupt such tissue. In some embodiments, all or a portion of surface 88 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, surface 88 may be rough, textured, porous, semi-porous, dimpled, knurled, toothed, grooved and/or polished to facilitate engagement and cutting of tissue.

Portion 82 defines an even, uninterrupted edge surface of thread form 78, and includes an even, solid surface relative to portion 80, which provides a variable configuration of thread form 78. Portion 82 extends along crest C forming an edge surface of thread form 78 that transitions from portion 80 and is configured to resist and/or prevent damage to tissue during insertion and/or engagement of bone screw 12 with tissue. Portion 82 is configured to resist and/or prevent damage to nerves, the dura and/or blood vessels. In some embodiments, portion 82 is continuous without any openings and/or cavities. In some embodiments, portion 82 includes a material having a closely compacted structure. In some embodiments, portion 82 includes a solid configuration, which may include a range of density including 0.5 through 10.5 grams per cubic centimeter. In some embodiments, portion 82 includes a density that is greater than a density of portion 80.

In some embodiments, thread 76 is fabricated to include a fine, closely-spaced and/or shallow configuration to facilitate and/or enhance engagement with tissue. In some embodiments, thread 76 is fabricated to include an increased pitch and an equal lead between thread turns than thread 28, as shown in FIG. 1. In some embodiments, thread 76 is fabricated to include a smaller pitch or more thread turns per axial distance than thread 28 to provide a stronger fixation with tissue and/or resist loosening from tissue. In some embodiments, thread 76 is fabricated to be continuous along portion 16. In some embodiments, thread 76 is fabricated to be continuous along portion 16. In some embodiments, thread 76 is fabricated to be intermittent, staggered, discontinuous and/or may include a single thread turn or a plurality of discrete threads. In some embodiments, portion 16 is fabricated to include penetrating elements, such as, for example, a nail configuration, barbs, expanding elements, raised elements, ribs, and/or spikes. In some embodiments, thread 46 is fabricated to be self-tapping or intermittent at distal tip 44. In some embodiments, distal tip 44 may be rounded. In some embodiments, distal tip 44 may be self-drilling. In some embodiments, distal tip 44 includes a solid outer surface.

For example, manipulation of bone screw 12, including rotation and/or translation causes lattice 56 to cut tissue and/or shave bone such that the cut tissue is guided and/or directed into openings 66 to promote bone growth and enhance fusion of bone screw 12. In some embodiments, external grating materials or biologics may be prepacked with bone screw 12. Core 54 is configured to allow bone screw 12 to respond to loads applied by vertebrae and/or other implants by providing selected deflection to resist and/or prevent bone screw 12 pull out from tissue.

In some embodiments, additive manufacturing includes 3-D printing, as described herein. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing or on-demand manufacturing. In some embodiments, portion 16 is manufactured by additive manufacturing, as described herein, and mechanically attached with surface 30 by, for example, welding, threading, adhesives and/or staking.

In one embodiment, one or more manufacturing methods for fabricating distal portion 16, proximal portion 14 and/or other components of bone screw 12 include imaging patient anatomy with imaging techniques, such as, for example, x-ray, fluoroscopy, computed tomography (CT), magnetic resonance imaging (MRI), surgical navigation, bone density (DEXA) and/or acquirable 2-D or 3-D images of patient anatomy. Selected configuration parameters of distal portion 16, proximal portion 14 and/or other components of bone screw 12 are collected, calculated and/or determined. Such configuration parameters can include one or more of patient anatomy imaging, surgical treatment, historical patient data, statistical data, treatment algorithms, implant material, implant dimensions, porosity and/or manufacturing method. In some embodiments, the configuration parameters can include implant material and porosity of distal portion 16 determined based on patient anatomy and the surgical treatment. In some embodiments, the implant material includes a selected porosity of distal portion 16, as described herein. In some embodiments, the selected configuration parameters of distal portion 16, proximal portion 14 and/or other components of bone screw 12 are patient specific. In some embodiments, the selected configuration parameters of distal portion 16, proximal portion 14 and/or other components of bone screw 12 are based on generic or standard configurations and/or sizes and not patient specific. In some embodiments, the selected configuration parameters of distal portion 16, proximal portion 14 and/or other components of bone screw 12 are based on one or more configurations and/or sizes of components of a kit of spinal implant system 10 and not patient specific.

For example, based on one or more selected configuration parameters, as described herein, a digital rendering and/or data of a selected distal portion 16, proximal portion 14 and/or other components of bone screw 12, which can include a 2-D or a 3-D digital model and/or image, is collected, calculated and/or determined, and generated for display from a graphical user interface, as described herein, and/or storage on a database attached to a computer and a processor (not shown), as described herein. In some embodiments, the computer provides the ability to display, via a monitor, as well as save, digitally manipulate, or print a hard copy of the digital rendering and/or data. In some embodiments, a selected distal portion 16, proximal portion 14 and/or other components of bone screw 12 can be designed virtually in the computer with a CAD/CAM program, which is on a computer display. In some embodiments, the processor may execute codes stored in a computer-readable memory medium to execute one or more instructions of the computer, for example, to transmit instructions to an additive manufacturing device, such as, for example, a 3-D printer. In some embodiments, the database and/or computer-readable medium may include RAM, ROM, EPROM, magnetic, optical, digital, electromagnetic, flash drive and/or semiconductor technology. In some embodiments, the processor can instruct motors (not shown) that control movement and rotation of spinal implant system 10 components, for example, a build plate, distal end 32 and/or laser emitting devices, as described herein.

Portion 14 is fabricated with threads 28 by a first manufacturing method, as described herein. Portion 14 is connected with a part, such as, for example, a build plate in connection with an additive forming process and a second manufacturing method for fabricating distal portion 16. Portion 16 is built up layer by layer and the melting process is repeated slice by slice, layer by layer, until the final layer of a material is melted and portion 16 is complete. Portion 16 is formed on distal end 32 to extend between an end 40 and end 42 according to instructions received from the computer and processor, and end 40 is fused with surface 30. In some embodiments, the material is subjected to direct metal laser sintering (DMLS®), selective laser sintering (SLS), fused deposition modeling (FDM), or fused filament fabrication (FFF), or stereolithography (SLA).

In some embodiments, portion 16 is fabricated in a configuration having a porosity via the additive manufacturing method, as described herein. In some embodiments, portion 16 is fabricated having a porosity with a porogen that is spheroidal, cuboidal, rectangular, elongated, tubular, fibrous, disc-shaped, platelet-shaped, polygonal or a mixture thereof. In some embodiments, a porosity of portion 16 is based on a plurality of macropores, micropores, nanopores structures and/or a combination thereof.

In some embodiments, bone screw 12 includes an implant receiver (not shown) connectable with head 20. In some embodiments, bone screw 12 can include various configurations, such as, for example, a posted screw, a pedicle screw, a bolt, a bone screw for a lateral plate, an interbody screw, a uni-axial screw, a fixed angle screw, a multi-axial screw, a side loading screw, a sagittal adjusting screw, a transverse sagittal adjusting screw, an awl tip, a dual rod multi-axial screw, midline lumbar fusion screw and/or a sacral bone screw. In some embodiments, the implant receiver can be attached by manual engagement and/or non-instrumented assembly, which may include a practitioner, surgeon and/or medical staff grasping the implant receiver and shaft 18 and forcibly snap or pop fitting the components together. In some embodiments, spinal implant system 10 comprises a kit including a plurality of bone screws 12 of varying configuration, as described herein. In some embodiments, bone screw 12 is selected from the kit and employed with a treatment at the surgical site.

In one embodiment, bone screw 12 is fabricated to define a passageway through all or a portion of shaft 18 such that bone screw 12 includes a cannulated configuration and a plurality of lateral fenestrations in communication with the passageway.

In assembly, operation and use, spinal implant system 10 is employed to treat an affected section of vertebrae. A medical practitioner obtains access to a surgical site including the vertebrae in any appropriate manner, such as through incision and retraction of tissues. The components of surgical system 10 including bone screw 12 are employed to augment a surgical treatment. Bone screw 12 can be delivered to a surgical site as a pre-assembled device or can be assembled in situ. Spinal implant system 10 may be may be completely or partially revised, removed or replaced.

Surgical system 10 may be used with surgical methods or techniques including open surgery, mini-open surgery, minimally invasive surgery and percutaneous surgical implantation, whereby the vertebrae is accessed through a mini-incision, or sleeve that provides a protected passageway to the area. Once access to the surgical site is obtained, a surgical treatment, for example, corpectomy and/or discectomy, can be performed for treating a spine disorder.

Bone screw 12 is connected with a surgical instrument, such as, for example, a driver (not shown) and is delivered to the surgical site. Bone screw 12 is manipulated including rotation and/or translation for engagement with cortical bone and/or cancellous bone. Manipulation of bone screw 12 causes lattice 56 to cut tissue and/or shave bone such that the cut tissue is guided and/or directed into openings 66 to promote bone growth and enhance fusion of bone screw 12. Core 54 is configured to allow bone screw 12 to respond to loads applied by vertebrae and/or other implants by providing selected deflection to resist and/or prevent bone screw 12 pull out from tissue.

Figure 4:
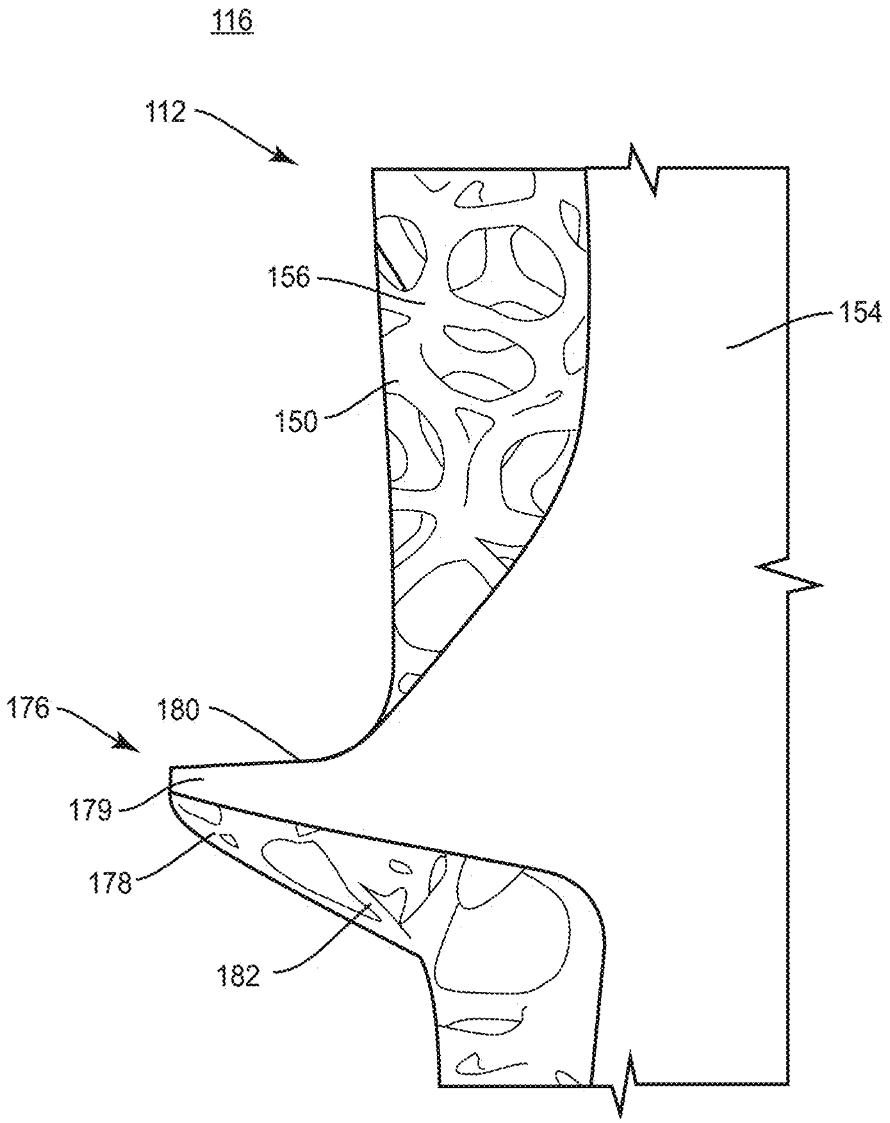
FIG. 4 is a break away cross section view of components of one embodiment of a system in accordance with the principles of the present disclosure.

In one embodiment, as shown in FIG. 4, spinal implant system 10, similar to the systems and methods described herein, includes a bone screw 112, similar to bone screw 12 described herein. Bone screw 112 includes portion 14, as described herein, and a portion 116.

Portion 116 includes a wall 150, similar to wall 50 described herein, having a non-solid configuration, as described herein, such as, for example, a lattice 156, similar to lattice 56 described herein. Wall 150 extends about a solid inner core 154, similar to core 54 as described herein. Portion 116 includes a thread 176. Thread 176 has a variable configuration, as described herein, and includes an external thread form 178. Thread form 178 includes a flank 179, similar to flank 79 as described herein.

Flank 179 has a variable configuration and includes a trailing edge 180 and a leading edge 182 to facilitate bone growth and/or fixation with tissue. Trailing edge 180 defines an even, uninterrupted edge surface of thread form 178, and includes an even, solid surface relative to portion 182, which provides a variable configuration of thread form 178. Trailing edge 180 transitions from inner core 154 such that inner core 154 and trailing edge 180 are homogenous. In some embodiments, trailing edge 180 is continuous without any openings and/or cavities, as described herein.

Leading edge 182 includes a lattice configuration to facilitate fusion of bone screw 112 with tissue, as described herein. Leading edge 182 transitions from lattice 156 such that wall 150 and leading edge 182 are homogenous. In some embodiments, leading edge 182 includes a trabecular configuration. In some embodiments, leading edge 182 is continuous without any openings and/or cavities, as described herein, and trailing edge 180 includes a lattice configuration.

In some embodiments, portion 116 is formed on distal end 32 by an additive manufacturing method, as described herein. In some embodiments, portion 116 is fabricated according to instructions received from the computer and processor based on the digital rendering and/or data of the selected configuration, via the additive manufacturing process, as described herein. Portion 116 is configured for fabrication on distal end 32 such that portion 116 is fused with surface 30, as described herein.

Figure 5:
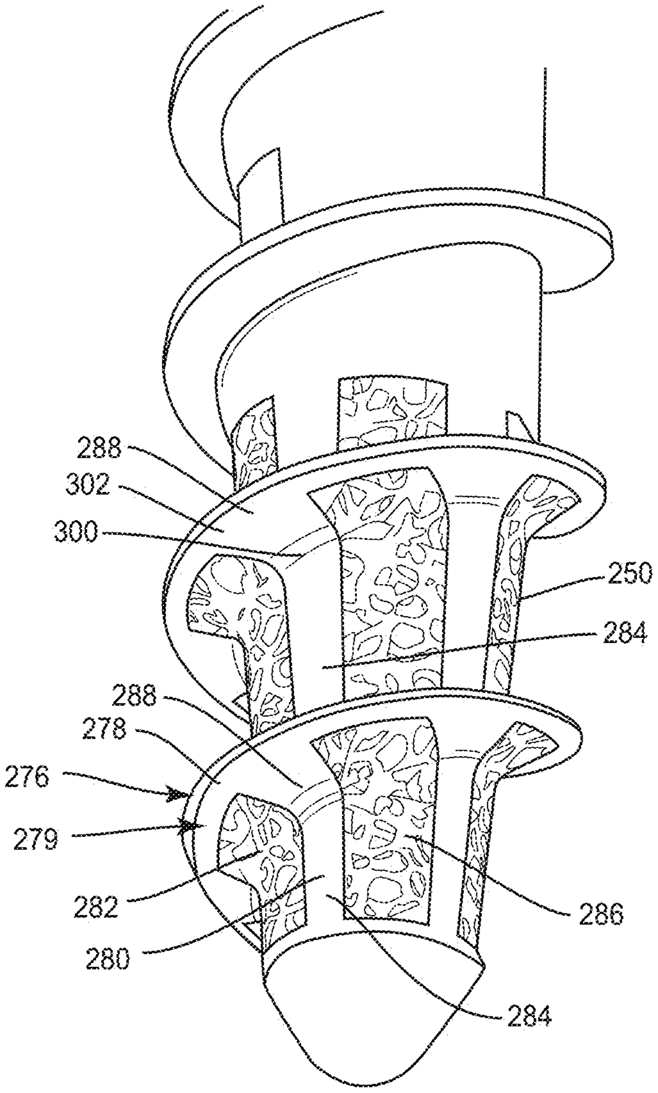
FIG. 5 is a break away perspective view of components of one embodiment of a system in accordance with the principles of the present disclosure.

In one embodiment, as shown in FIG. 5, spinal implant system 10, similar to the systems and methods described herein, includes a bone screw 212, similar to bone screw 12 described herein. Bone screw 212 includes portion 14, as described herein, and a portion 216.

Portion 216 includes a variable configuration, as described herein, and includes a wall 250. Wall 250 extends about a solid inner core 254, similar to core 54 as described herein. Portion 216 includes a thread 276 having an external thread form 278. Thread form 278 includes a flank 279, similar to flank 79 as described herein.

Wall 250 has a variable configuration and includes a portion 280 and a portion 282 to facilitate bone growth and/or fixation with tissue. Portion 280 includes a plurality of struts 284 that extend along portion 216. Struts 284 are circumferentially disposed about portion 216 and define a cavity 286 therebetween. Struts 284 include an even, solid surface relative to portion 282, as described herein. Struts 274 transition from inner core 254 to reinforce thread 276 to resist and/or prevent pull-out.

Struts 284 include a tapered flange 288. Flange 288 extends along all or a portion of flank 279, which provides a variable configuration of thread form 278. Flange 288 extends between an end 300 and an end 302. Flange 288 includes an increase in diameter from end 300 to end 302 to support and/or strengthen thread form 278.

Portion 282 includes lattice 286, similar to lattice 56 as described herein. Portion 282 is disposed with cavities 286 such that lattice 286 is non-continuous along portion 216 forming the variable configuration of wall 250. Lattice 286 extends along all or a portion of flank 279, which provides a variable configuration of thread form 278 with struts 284. In some embodiments, portion 282 includes a trabecular configuration, as described herein.

In some embodiments, portion 216 is formed on distal end 32 by an additive manufacturing method, as described herein. In some embodiments, portion 216 is fabricated according to instructions received from the computer and processor based on the digital rendering and/or data of the selected configuration, via the additive manufacturing process, as described herein. Portion 216 is configured for fabrication on distal end 32 such that portion 216 is fused with surface 30, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone screw comprising:

a shaft defining a longitudinal axis, the shaft comprising a first portion and a second portion, a threaded section extending along at least part of the first portion and the second portion, the second portion comprising an inner core and a wall disposed about the inner core;

at least a portion of the wall comprising a trabecular configuration comprising lattices;

wherein at least a portion of the wall defines a plurality of spaced apart struts around the second portion, and wherein the lattices are positioned between at least some of the struts, the struts comprising a solid surface relative to the lattices;

wherein the struts span at least partially between threads of the second portion; and wherein a portion of the threaded section extends outwardly from the wall.

2. The bone screw of claim 1, wherein the threaded section comprises a first segment disposed along the first portion and a second segment disposed along the second portion.

3. The bone screw of claim 2, wherein the first segment of the threaded section comprises continuous threads.

4. The bone screw of claim 2, wherein the first segment of the threaded section is disposed adjacent to a proximal end of the shaft.

5. The bone screw of claim 2, wherein threads of the second segment are intermittent, staggered or discontinuous.

6. The bone screw of claim 2, wherein the threaded section comprises non-porous threads around the first segment.

7. The bone screw of claim 1, further comprising a distal tip with a solid outer surface.

8. The bone screw of claim 7, wherein the distal tip comprises threads.

9. The bone screw of claim 8, wherein the threads of the distal tip are self-tapping or intermittent.

10. The bone screw of claim 7, wherein the distal tip is tapered.

11. The bone screw of claim 1, wherein the lattices define at least a portion of the threaded section around the second segment.

12. The bone screw of claim 1, wherein the threaded section comprises a porous area that at least partially overlaps with the trabecular configuration of the wall.

13. The bone screw of claim 1, wherein the trabecular configuration extends from an outer portion of the wall to the inner core.

14. A bone screw comprising:

a shaft defining a longitudinal axis, the shaft including a first portion and a second portion, a threaded section disposed along the first portion and the second portion, the second portion comprising an inner core and a wall disposed about the inner core;

at least a portion of the threaded section extending outwardly from the wall around the second portion of the shaft, the wall comprising a surface, a plurality of spaced apart struts around the second portion and a plurality of lattices disposed between the struts, the struts comprising a solid surface relative to the lattices, the lattices comprising a plurality of nodes and openings;

wherein the nodes and openings of the lattices are disposed in a predetermined orientation;

wherein the struts span at least partially along the longitudinal axis between consecutive threads of the second portion;

wherein the threads of the second section are discontinuous; and wherein the lattices extend between discontinuous parts of the threads of the second section.

15. The bone screw of claim 14, wherein the nodes and openings are disposed in rows, columns or a random configuration.

16. The bone screw of claim 14, wherein the nodes and openings are disposed in a series orientation or a parallel orientation.

17. A bone screw comprising:

a shaft defining a longitudinal axis, the shaft including at least a first portion and a second portion, the second portion comprising an inner core and a wall disposed about the inner core, the wall comprising a surface, the wall defining a plurality of spaced apart struts and lattices positioned between the struts around the second portion, the struts comprising a solid surface, and a threaded section disposed along the first portion and the second portion, a portion of the threaded section extending from the wall, the struts and lattices disposed in a predetermined orientation along the wall;

wherein the struts span at least partially along the longitudinal axis between consecutive threads of the second portion; and wherein the second portion is fabricated on an end of the first portion by an additive manufacturing method comprising 3-D printing.

18. The bone screw of claim 17, wherein the predetermined orientation comprises at least one layer of lattices disposed in a parallel orientation or in a stepped orientation along the wall.

19. The bone screw of claim 17, wherein the shaft and the threaded section are manufactured by the additive manufacturing method comprising 3-D printing.

* * * * *